United States Patent [19]

Dussourd d'Hinterland et al.

[11] Patent Number: 4,501,693

[45] Date of Patent: Feb. 26, 1985

[54] METHOD OF PREPARING IMMUNOSTIMULANT PROTEOGLYCANS WHICH INDUCE PRODUCTION OF INTERFERON, PROTEOGLYCANS OBTAINED AND PHARMACEUTICAL COMPOSITIONS CONTAINING THEM

[75] Inventors: Lucien Dussourd d'Hinterland; Gérard Normier; Anne-Marie Pinel, all of Castres, France

[73] Assignee: Pierre Fabre S.A., Paris, France

[21] Appl. No.: 471,641

[22] Filed: Mar. 3, 1983

[30] Foreign Application Priority Data

Mar. 9, 1982 [FR] France .................. 82 03921

[51] Int. Cl.³ .............. A61K 37/102; A61K 39/108; A61K 39/40; C07G 7/00
[52] U.S. Cl. ................. 260/112 R; 260/112 B; 424/89; 435/68; 435/259
[58] Field of Search .............. 260/112 R, 112 B; 435/68, 259; 424/89

[56] References Cited

U.S. PATENT DOCUMENTS

| | | | |
|---|---|---|---|
| 3,855,197 | 12/1974 | Hirsch et al. | 260/112 R |
| 3,976,544 | 8/1976 | Adam et al. | 435/259 X |
| 4,036,953 | 7/1977 | Adam et al. | 435/259 X |
| 4,154,821 | 5/1979 | Drovet et al. | 260/112 R X |
| 4,297,272 | 10/1981 | D'Hinterland et al. | 260/112 R |
| 4,356,171 | 10/1982 | Zalisz et al. | 260/112 R X |
| 4,412,946 | 11/1983 | Zalisz et al. | 260/112 R |
| 4,451,446 | 5/1984 | Vandevelde et al. | 260/112 R X |

OTHER PUBLICATIONS

Organic Chemistry of Biological Compounds, Barker, p. 128, (1971).
Biochemistry, Lehninger, p. 236, (1971).
Microbiology, Lee, pp. 199–201, (1983).

*Primary Examiner*—Howard E. Schain
*Attorney, Agent, or Firm*—Oblon, Fisher, Spivak, McClelland & Maier

[57] ABSTRACT

The present invention relates to a method of preparing bacterial membranous proteoglycans with an action which induces interferon from soluble membranous proteoglycans of a strain of gram-negative bacterium, wherein the soluble membranous proteoglycans of a strain of gram-negative bacterium are hydrolyzed by lysozyme and the proteoglycans with a molecular weight between 200,000 and 400,000 are separated from the hydrolysis product.

The products obtained are useful as a medicament.

8 Claims, 4 Drawing Figures

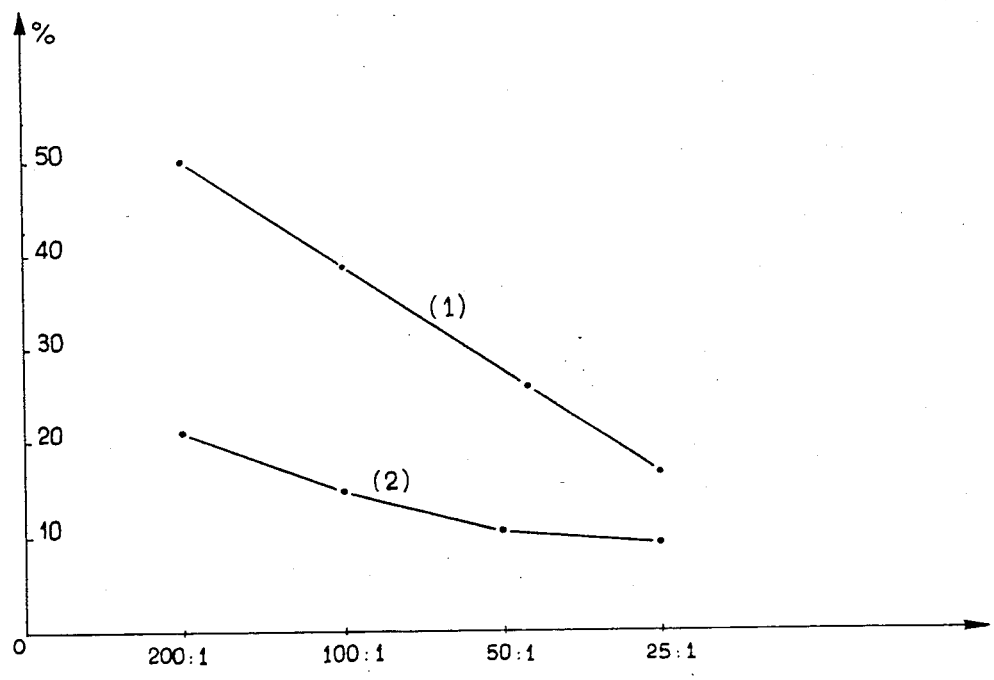
FIG_1

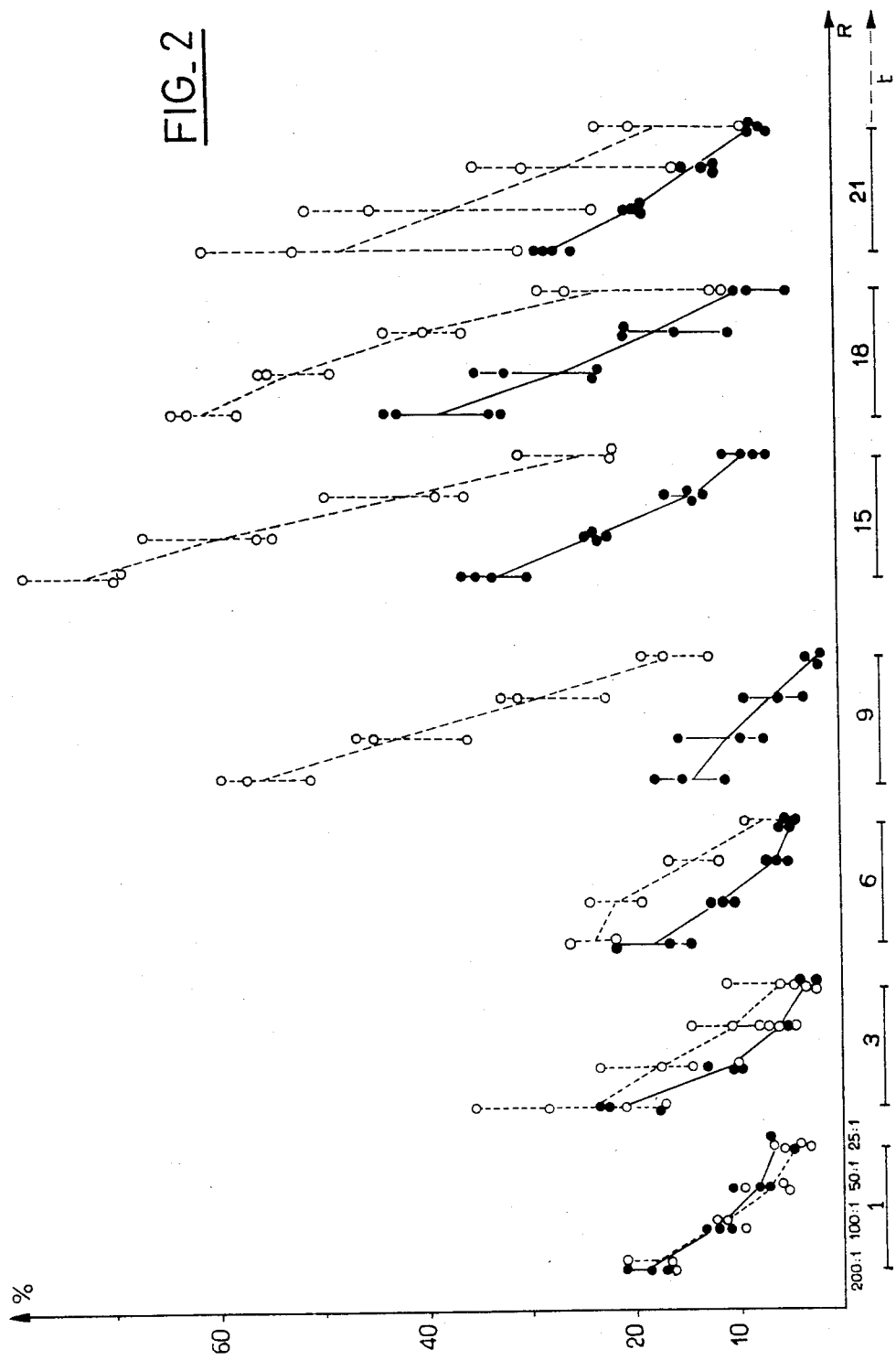
FIG._2

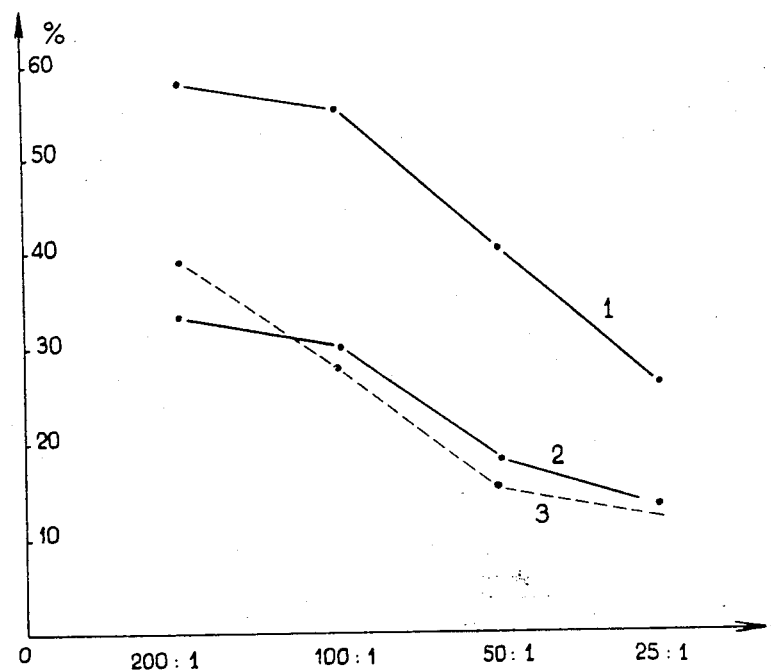
FIG_3
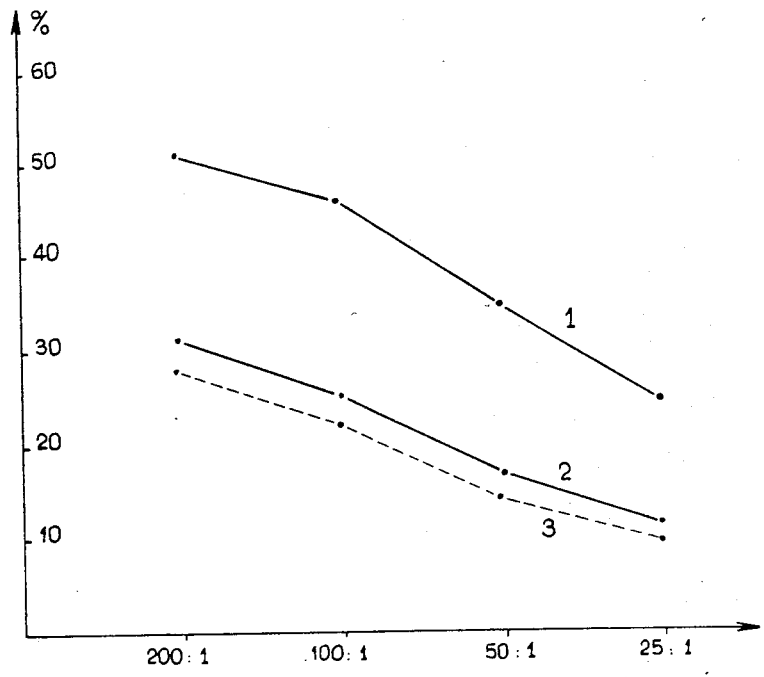
FIG_4

METHOD OF PREPARING IMMUNOSTIMULANT PROTEOGLYCANS WHICH INDUCE PRODUCTION OF INTERFERON, PROTEOGLYCANS OBTAINED AND PHARMACEUTICAL COMPOSITIONS CONTAINING THEM

The present invention relates to a proteoglycanic fraction isolated from bacterial membranes as well as a method for its preparation and its use as an immunostimulant, especially for the activation of N.K. (Natural Killer) cells known for their cytotoxic power against tumoral cells.

French Pat. No. 78 35649 filed Dec. 19, 1978 under the name of the applicant described the preparation of detoxified membranous proteoglycans from gram-negative bacteria and their use as an adjuvant in vaccines.

The present invention describes, starting with this type of membranous proteoglycan coming in particular from a strain of Klebsiella pneumoniae, the isolation of a proteoglycanic fraction possessing immunostimulant qualities, the most remarkable of which is to activate sharply the stimulation of N.K. cells.

The method of the present invention, which allows bacterial membranous proteoglycans with an immunostimulant activity, especially one which induces production of interferon, to be prepared from soluble membranous proteoglycans of a strain of gram-negative bacterium, entails hydrolyzing the soluble membranous proteoglycans of a strain of gram-negative bacterium by the lysozyme and then separating proteoglycans with a molecular weight between 200,000 and 400,000 from the hydrolysis product.

The soluble membranous proteoglycans used as initial products in the method of the invention are preferably prepared according to the methods described in French Pat. No. 78 35649. In the method of French Pat. No. 78 35649 the essential step consists of treating the raw membranous proteoglycans, separated by one of the known methods, in an aqueous medium by a base or a hypobromite and in recovering the aqueous phase containing the soluble proteoglycans.

Other characteristics of this method can be found in the preceeding patent, the teachings of which are incorporated into the present description by way of reference.

The separation of the proteoglycans with a molecular weight between 200,000 and 400,000, which constitute the active fraction according to the invention, can be accomplished by any method, in particular by using a chromatography on a molecular sieve, e.g. on a Sepharose CL 2B column of gel.

The treatment by the lysozyme hydrolyzes the N-acetyl muramyl-(1-4)-N-acetyl glucosamine bonds of the proteoglycans by reducing in this manner the molecular weight of these fractions. The duration of this hydrolysis is preferably between 10 minutes and 1 hour and in general on the order of 30 minutes. Before submitting the hydrolysis product to chromatographic fractionation, it is interesting to eliminate the lysozyme and the different salts or compounds present.

The soluble proteoglycans are preferably delipidated, e.g. by means of one or several lipid solvents, before being subjected to the action of the lysozome.

From the gram-negative bacteria which can be used, it is preferable to use in particular Klebsiella pneumoniae, Serratia marcescens and Escherichia Coli and especially the strain of Klebsiella pneumoniae which is a non-capsulated strain isolated by the Pierre Fabre Center for Immunology and Biology and deposited with the National Collection for the Culture of Microorganisms (CNCM) under the number 145-I-IP.

The proteoglycanes obtained in this manner have the following physico-chemical characteristics:

| | |
|---|---|
| molecular weight between | 200,000 and 400,000 |
| hexose content | 8 and 10% |
| galactose content | 22 and 28% |
| hexosamine content | 3 and 4% |
| uronic acid content | 4 and 6% |
| protein content | 35 and 50% |

The present invention also relates to the use of these proteoglycans a medicament. As a matter of fact, these proteoglyans have valuable immunostimulant qualities.

These immunostimulant qualities have been demonstrated by injection and orally in mice.

Thus, a strong activation of N.K. Cells, significant ($P > 0.01$), on a lymphome induced by Moloney virus in mice was demonstrated for these products. This action is inhibited by an anti-interferon ($\alpha$-IF), which shows that the activation of the N.K. Cells by this fraction is due to an inductive effect of interferon.

In young animals the proteoglycans stimulate both N.K. and pre-N.K. cells.

A stimulation of the synthesis of DNA in vitro by splenic mouse cells is also observed in a fashion proportional to the dose and a potentiation of the early antibody response to bovine serum albumin (BSA).

In addition, a very strong stimulation of the macrophages is demonstrated in the following five systems:
- chemiluminescence of human granulocytes in vitro,
- phagocytosis in vitro of protein A marked by 125 I,
- study of the nature of the macrophages activated (Ia+ or Ia−),
- test of the elimination of the colloidal carbon in vivo,
- protection test against Candida albicans.

In all the systems studied, significant modifications of the cellular activity are observed which are expressed in vivo by a marked increase or the elimination of carbon and an increased resistance to infection by Candida albicans. A considerable impact was demonstrated on the first stages of the phagocytosis of human granulocytes by a chemiluminescence test. On the macrophages by a measurement in vitro after activation in vivo, increase of the phagocytic qualities by simultaneously inducing a more primitive phenotype.

The following examples illustrate a method of preparing proteoglycans according to the invention.

EXAMPLE 1

Preparation of soluble membranous proteoglycans (a) Isolution of raw membranous proteoglycans The biomass of the Klebsiella pneumoniae strain 145-I-IP is dispersed in a Tris—HCl 0.01M pad, pH 7.0, containing frozen NaCl 0.15M, then subjected to a mechanical crushing to break the cell walls.

The bacterial lysate is clarified by a centrifugation of 10 minutes at 7,500 g, then the substance floating on the surface is centrifuged for 45 minutes at 30,000 g.

The residue is dispersed in an aqueous solution of NaCl 0.15M. The suspension is clarified again for 10 minutes at 7,500 g, then centrifuged 45 minutes at 30,000 g.

The residue is placed in distilled water, then subjected again to a centrifuging cycle of 7,500 g, then 30,000 g.

The residue of raw membranous proteoglycans is then placed in one fourth of the initial volume of distilled water, the suspension is clarified 10 minutes at 7,500 g and the substance floating on top is lyophilized.

(b) Extraction of the soluble membranous proteoglycans

The lyophilized, raw membranous proteoglycans are dispersed in NaOH (0.1M), then subjected to a hydrolysis performed for 1 hour at 56° C. After cooling, the suspension is neutralized by diluted HCl, then dialyzed 24 hours against distilled water. The suspension is then clarified by centrifugation 45 minutes at 30,000 g, then the substance floating on top is filtered on a 0.22 membrane. The filtrate is lyophilized.

EXAMPLE 2

Preparation of the immunostimulant fraction (a) Delipidation of the soluble membranous proteoglycans The lyophilizate of soluble membranous proteoglycans obtained according to Example 1 is delipidated by a first extraction of 2 hours at 25° C. in a chloroform/methanol (2/1) mixture.

After drying on a no. 4 fritted glass, the residue is extracted for 2 hours at 25° C. in an ether/ethanol (1/3) mixture.

After drying on no. 4 fritted glass, the residue is dried in a vacuum.

(b) Treatment by lysozyme

The dry residue of soluble delipidated proteoglycans is dissolved in a Tris—HCl 0.015M pod, pH 8.0, containing EDTA, Na$_2$ 0.008M and 80 mg/l lysozyme.

After 30 minutes of incubation at 25° C., the solution is chromatographed on a Biogel P$_{30}$ column in distilled water.

The first peak eluted in the exclusion volume is collected, then dialysed against distilled water.

After filtration on a 0.92 membrane, the filtrate is lyophilized.

(c) Chromatographic fractionation

The preceeding lyophilizate is dissolved in a Tris-HCl 0.01M pod, pH 7.0, then subjected to a fractionation by molecular sieve chromatography on a column of gel Sepharose CL 2B balanced by the same pad.

The fractions corresponding to the peak containing the immunostimulant activity with a molecular weight between 200,000 and 400,000 are regrouped, then dialyzed against distilled water.

The dialyzate is sterilized by filtration on a 0.22 membrane, then sterilly lyophilized.

The lyophilizate constitutes the immunostimulant proteoglycanic fraction which will be used in the following examples.

The proteoglycanic fraction as it is isolated in a homogenous peak on Sepharose CL 2B presents the following average analytic characteristics:

| | |
|---|---|
| molecular weight | (= 300,000) |
| hexose content | 9.3% |
| galactose content | 25.2% |
| hexosamine content | 4.5% |
| uronic acid content | 5.3% |
| protein content | 42.5% |
| ARN content | <0.05% |
| ADN content | <0.02% |
| fatty acid content | <<1% |

The following examples are intended to demonstrate the immunostimulant qualities of the proteoglycans obtained in Example 2.

All of the N.K. tests described below were conducted according to the general protocol described in R. Kiessling and H. Wigzell, Immunol. Rev. 44, 165, 1979.

EXAMPLE 3

Activation of N.K. cells by injection

Animals: CBA/J mice 4 months old (moles)
target cells: YAC- 1 sensitive to N.K. (lymphome induced by Moloney virus in mice).

Protocol

The mice receive 15 μg of the proteoglycanic fraction in 0.2 ml PBS intraperitoneally.

The test is performed 24 hours later.

The measured results are shown in FIG. 1.

These graphs show the percentage of lysis of the target cells as a function of the relationship by number of effector cells (that is, the N.K. cells) to the target cells.

In FIG. 1 curve 1 corresponds to the animals treated and curve 2 corresponds to a control group.

A strong activation of the N.K. cells in the animals treated in relation to the control animals was determined.

The response is significant (P>0.01) in relation to the control values in this test.

EXAMPLE 4

Oral activation of N.K. cells

Animals: CBA/H mice
target cells: YAC cells sensitive to N.K. (Moloney lymphome) -P 815 cells non-sensitive to N.K. (DBA/2 mastocytome).

Protocol

Each mouse received one oral dose per day of 15 μg proteoglycanic fraction for 14 days. An identical dose of 15 μg was then administered also per os on the 18th day.

Results (a) YAC cells (sensitive)

The results measured are shown in the graph of FIG. 2.

This graph shows the percentage of lysis of the target cells as a function of the relationship between the effector cells and the target cells but at different times. Thus, t indicates the number of days elapsed since the start of the treatment and for each day the percentage of lysis was measured with four different dilutions: 200/1, 100/1, 50/1 and 25/1. Each dot represents the average of a certain number of tests and the results observed for three groups of experiments are shown. The white dots represents the results observed for the treated animals and the black dots the results for the control animals.

The results are extremely sharp, and a highly significant increase of the N.K. activity is determined. This activity, which can be detected from the 3rd day, becomes very great on the 6th day and the 9th day and is maintained at a very high level for the entire duration of the experimentation (21 days).

(b) P815 cells (non-sensitive)

The results observed show that in contrast to the N.K. positive test using YAC cells as target there is no significant cytotoxicity which can be discerned at any moment of the experiment.

EXAMPLE 5

Verification of the generation of interferon by the proteoglycanic fraction

Animals: CBA/J mice 5 months old (males)
target cells: -YAC- 1 sensitive to N.K. -Nulli Teratoma sensitive to N.K.

Protocol

The N.K. test is performed according to the customary protocol with animals which receive the proteoglycanic fraction by itself or with anti-interferon ($\alpha$-IF).

The results observed are shown in the graphs of FIGS. 3 and 4 set up as is indicated in Example 3.

The graph of FIG. 3 shows the results observed for the YAC target cells:
curve 1 corresponds to the treated animals.
curve 2 corresponds to the non-treated animals.
curve 3 corresponds to the animals treated both with proteoglycans and with anti-interferon.

The graph of FIG. 4 shows the same type of results but for Nulli target cells.

These results clearly indicate that the proteoglycanic fraction very strongly activates N.K cells via a generation of interferon.

We claim:

1. A method of preparing bacterial membranous proteoglycans which induce production of interferon from soluble membranous proteoglycans of a strain of gram-negative bacterium, which comprises hydrolyzing the soluble membranous proteoglycans of a strain of gram-negative bacterium by lysozyme, and separating the proteoglycans with a molecular weight between 200,000 and 400,000 from the hydrolysis product.

2. The method according to claim 1, wherein the proteoglycans are separated by chromatography on a molecular sieve.

3. The method according to claim 2, wherein the proteoglycans are separated by chromatography on a Sepharose CL 2B gel.

4. The method according to one of claims 1 to 3, wherein the soluble proteoglycans are delipidated before hydrolysis by the lysozyme.

5. The method according to claim 4, wherein the delipidation is performed by extraction with one or more lipid solvents.

6. The method according to claim 1, wherein the gram-negative bacterium is selected from the group consisting of *Klebsiella pneumoniae, Serratia marcescens,* or *Escherichia coli.*

7. The method according to claim 6, wherein the gram-negative bacterium is a *Klebsiella pneumoniae.*

8. The method of preparing bacterial membranous proteoglycans according to claim 1, wherein said hydrolysis is effected for about 10 minutes to an hour.

* * * * *